US009897629B2

United States Patent
Cen et al.

(10) Patent No.: US 9,897,629 B2
(45) Date of Patent: Feb. 20, 2018

(54) BIOELECTRIC SIGNAL DETECTING CIRCUITS, LEAD WIRE DETECTING CIRCUITS AND MEDICAL DEVICES

(71) Applicant: SHENZHEN MINDRAY BIO-MEDICAL ELECTRONICS CO., LTD., Shenzhen (CN)

(72) Inventors: Jian Cen, Shenzhen (CN); Qiling Liu, Shenzhen (CN); Xiaoyu Wu, Shenzhen (CN); Bing Wang, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 520 days.

(21) Appl. No.: 14/525,016

(22) Filed: Oct. 27, 2014

(65) Prior Publication Data
US 2015/0042315 A1    Feb. 12, 2015

Related U.S. Application Data

(63) Continuation of application No. PCT/CN2013/074487, filed on Apr. 22, 2013.

(30) Foreign Application Priority Data

Apr. 25, 2012   (CN) .......................... 2012 1 0124768

(51) Int. Cl.
*A61B 5/04* (2006.01)
*G01R 15/00* (2006.01)
(Continued)

(52) U.S. Cl.
CPC ................ *G01R 15/00* (2013.01); *A61B 5/04* (2013.01); *A61B 5/04004* (2013.01);
(Continued)

(58) Field of Classification Search
None
See application file for complete search history.

(56) References Cited

U.S. PATENT DOCUMENTS 5,054,496 A  * 10/1991 Wen .................... A61B 5/04085
                                                      600/509
2003/0083701 A1    5/2003 Ericksen et al.

FOREIGN PATENT DOCUMENTS

| CN | 85108601 A   | 9/1986 |
| CN | 1611185 A    | 5/2005 |
| CN | 102068247 A  | 5/2011 |

* cited by examiner

*Primary Examiner* — Ankit D Tejani
(74) *Attorney, Agent, or Firm* — Kory D. Christensen; Polsinelli LLP

(57) ABSTRACT

This disclosure relates to bioelectric signal detecting circuits, lead wire detecting circuits and medical devices. The lead wire detecting circuit may include a reference voltage generator, at least one comparator, and a logic control module, wherein input ends of the comparator are connected to an output end of the reference voltage generator and an signal output end of a lead wire, respectively, for inputting a reference voltage and a lead signal, and the comparator compares the lead signal with the reference voltage and changes an output voltage at an output end of the comparator according to a comparison result; wherein an input end of the logic control module is connected to the output end of the comparator, and the logic control module determines whether the lead wire is in a connected state or disconnected state by the output voltage at the output end of the comparator.

9 Claims, 4 Drawing Sheets

(51) Int. Cl.
*A61B 5/0428* (2006.01)
*A61B 5/0476* (2006.01)
*G01R 1/067* (2006.01)
*G01R 19/00* (2006.01)

(52) U.S. Cl.
CPC .......... *A61B 5/0428* (2013.01); *A61B 5/0476* (2013.01); *G01R 1/067* (2013.01); *G01R 19/0084* (2013.01)

BIOELECTRIC SIGNAL DETECTING CIRCUITS, LEAD WIRE DETECTING CIRCUITS AND MEDICAL DEVICES

TECHNICAL FIELD

This disclosure relates generally to medical devices. Particularly, this disclosure relates to bioelectric signal detecting circuits, lead wire detecting circuits, and associated medical devices.

BACKGROUND

Physiological activities of certain organs (such as the heart and cerebrum) may be reflected by bioelectricity waves. The process of electrocardiography (ECG) or electroencephalography (EEG), in which lead wires are connected to the patient's chest or cerebrum, may assist a doctor in judging tissue lesions. A poor connection or even disconnection of a lead wire (i.e., when the lead wire has a disconnected state) will cause a detection failure. In existing lead wire detection techniques, each lead wire is connected to a constant current resource or a bias circuit, respectively, in which the bias circuit may include a voltage source and a megohm resistor. For example, in ECG detection, when a lead wire is connected to a human body, the human body impedance is much less than the output impedance of the corresponding bias circuit, and the voltage drop to the human impedance is small, so the voltage at the ECG front end is close to 0V, and the ECG measurement would not be affected. When the lead wire is disconnected, the impedance is infinity and the lead wire is driven to a certain voltage by the bias circuit. So the voltage at the ECG input channel would significantly vary when the lead wire is in a connected state or disconnected state. A system usually comprises an Analog-to-Digital Converter (ADC), and usually the ADC is used for cyclically sampling the voltage of the ECG input channel. A voltage threshold, which is between the voltages at the ECG input channel when the lead wire is in a connected state and disconnected state, is selected, and the connection status of the lead wire is determined by comparing sampled voltages with the voltage threshold. This approach requires a higher sampling rate of the ADC and increases the burden on the ADC, presenting system design difficulties and higher costs.

SUMMARY

Disclosed herein are embodiments of bioelectric signal detecting circuits, lead wire detecting circuits, and associated medical devices. In one aspect, a bioelectric signal detecting circuit may include: at least one lead wire, which comprises a contact end for contacting with a human body and a signal output end; at least one bias circuit, wherein each bias circuit corresponds to one of the at least one lead wire and the bias circuit is connected to the signal output end of the one of the at least one lead wire; a reference voltage generator for outputting a reference voltage; at least one comparator, wherein input ends of the comparator are connected to an output end of the reference voltage generator and the signal output end of the lead wire, respectively, for inputting a reference voltage and a lead signal, and the comparator compares the lead signal with the reference voltage and changes an output voltage at an output end of the comparator according to a comparison result; a logic control module, wherein an input end of the logic control module is connected to the output end of the comparator, and the logic control module determines whether the lead wire is in a connected state or disconnected state according to at least the output voltage at the output end of the comparator.

In still another aspect, a lead wire detecting circuit may include: a reference voltage generator for outputting a reference voltage; at least one comparator, wherein input ends of the comparator are connected to an output end of the reference voltage generator and a signal output end of a lead wire, respectively, for inputting a reference voltage and a lead signal, and the comparator compares the lead signal with the reference voltage and changes an output voltage at an output end of the comparator according to a comparison result;

a logic control module, wherein an input end of the logic control module is connected to the output end of the comparator, and the logic control module determines whether the lead wire is in a connected state or disconnected state by the output voltage of the comparator.

In still another aspect, a medical device may include: at least one lead wire, which comprises a contact end for contacting with a human body and a signal output end; at least one bias circuit, wherein each bias circuit corresponds to one of the at least one lead wire and is connected to the signal output end of the one of the at least one lead wire; and a lead wire detecting the circuit as previously described.

In this disclosure, the lead wire detecting circuit may be realized by comparators and a logic control module. The structure of the circuit is simple, inexpensive, and may be easily integrated into a chip.

DETAILED DESCRIPTION

In the following embodiments, a comparator compares an output signal of a lead wire with a threshold preset. When the lead wire is in a disconnected state, the input voltage of the comparator is equal to the threshold preset, and the output of the comparator is one status; when the lead wire is in a connected state, the input voltage of the comparator is equal to the voltage drop to human tissue, which is close to 0V, and the output of the comparator is another status. Thus, the connected state or disconnected state of the lead wire may be determined by the output status of the comparator.

Figure 1:
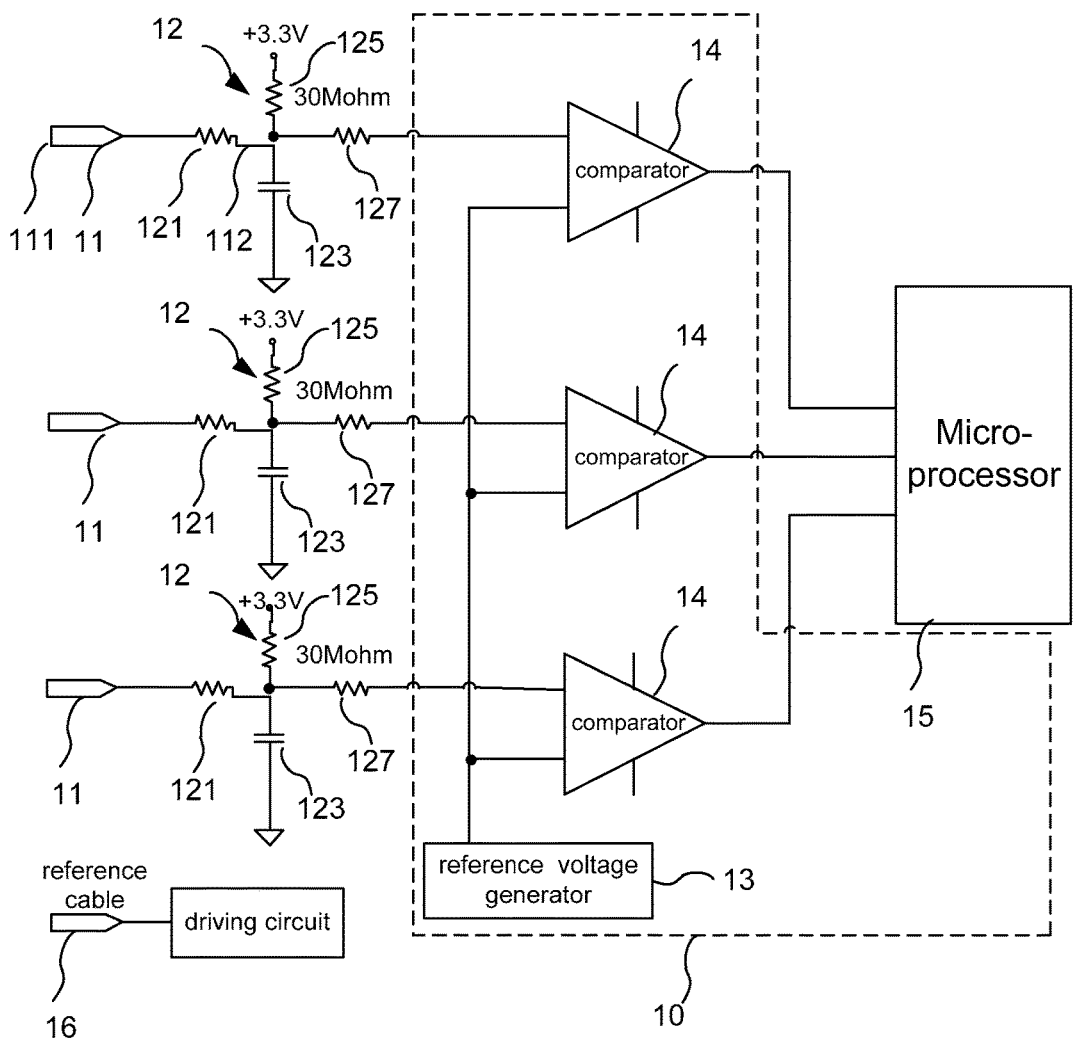
FIG. 1 shows a schematic diagram of a bioelectric signal detecting circuit according to an embodiment.

As shown in FIG. 1, a bioelectric signal detecting circuit may include three lead wires 11 used for normal testing, three bias circuits 12, and one lead wire detecting circuit 10. The lead wire detecting circuit 10 may include a reference voltage generator 13, a comparator 14 and a logic control module. The logic control module is used to implement a logic function, which may be realized as logic gates, an MCU (Microprogrammed Control Unit), an FPGA (Field Programmable Gate Array), and so on. In the illustrated embodiment, the logic control module may include a microprocessor 15.

The lead wire 11 may include a contact end, used for contact with the human body, and a signal output end 112. During human tissue signal acquisition, the contact end 111 contacts with the human body by way of gripping or pasting, then the signal output end 112 outputs a bioelectrical signal recognized by the lead wire 11. There is one-to-one correspondence between the bias circuits 12 and the lead wires 11, and each bias circuit 12 is connected to the signal output end 112 of corresponding lead wire 11. The bias circuit 12 may be realized by a constant current source or by a voltage source and a megohm resistor, which is connected to the voltage source. For example, the megohm resistor may be connected between the voltage source and the signal output end 112 of the lead wire 11, which may provide a bias voltage to the detecting circuit when the lead wire 11 is disconnected. In an embodiment, as shown in FIG. 1, the bias circuit 12 may include a bias resistor 125 and a 3V voltage, which provides bias voltage through the bias resistor 125. The output signal of the lead wire 11, which is the bioelectric signal, is coupled to an input end of the comparator 14 by resistors 121, 127 and a capacitance 123.

The reference voltage generator 13 generates and outputs a reference voltage, which is the threshold used for judging whether the lead wire is in a connected state or disconnected state and which may be predefined as needed. Two input ends of the comparator 14 are connected to the output end of the reference voltage generator 13 and the signal output end 112 of the lead wire, respectively, and the output end of the comparator 14 is connected to the microprocessor 15; for example, the output end of the comparator 14 is connected to the input/output interface (IO port) of the microprocessor 15. The comparator 14 compares real-time lead signals outputted by the signal output end 112 of the lead wire 11 with the reference voltage and changes in output voltage at the output end of the comparator 14 by the comparison result. For example, when the lead signal is greater than or equal to the reference voltage, which means one input of the comparator 14 is the bias voltage, the comparator 14 outputs a first voltage. When the lead signal is smaller than the reference voltage, which means one input of the comparator 14 is the bioelectric voltage, the comparator 14 outputs a second voltage. The microprocessor 15 determines whether the lead wire 11 is in a connected state or disconnected state by the output of the comparator. For example, if the microprocessor 15 reads the input of the IO port in a first time interval—e.g., 1 s—the lead wire is determined to be in a disconnected state when the input of the IO port read is equal to the first voltage, and the lead wire is determined to be in a connected state when the input of the IO port read is equal to the second voltage.

When the lead wire 11 is in a connected state, the human impedance accessed by the lead wire 11 is much less than the impedance of the bias circuit 12, so the voltage drop to the human impedance is small, and the voltage at the signal output end 112 of the lead wire 11 is basically equal to the bioelectric voltage. When the lead wire 11 is in a disconnected state, the impedance accessed by the lead wire 11 is infinite, so the voltage at the signal output end 112 of the lead wire 11 is much higher than normal ECG amplitude. Therefore, the condition of whether the lead wire 11 is in a connected state or disconnected state may be recognized by the voltage at the signal output end 112 of the lead wire 11. In one embodiment, the comparator 14 compares the voltage at the signal output end 112 of the lead wire 11 and the threshold (i.e., the reference voltage). If the voltage at the signal output end 112 of the lead wire 11 is greater than or equal to the threshold, the output of the comparator 14 is "1" (high level), which indicates one status; if the voltage at the signal output end 112 of the lead wire 11 is less than the threshold, the output of the comparator 14 is "0" (low level), which indicates another status. The microprocessor 15 determines whether the lead wire 11 is in a connected state or disconnected state by checking to see whether the output of the comparator is "1" or "0"; thus the output of the lead wire 11 does not need to do any analog-to-digital conversion before being compared with the threshold. In one embodiment, an ADC is not necessary, so hardware complexity and the requirement for ADC are reduced. In one embodiment, the comparator 14 is necessary, but it is cheap and may be integrated into a chip easily.

Because of large external frequency interference or poor contact of the lead wire, 50 Hz or 60 Hz interference may occur on the lead wire. When the lead wire is in a disconnected state, a fixed DC voltage is superposed on the lead signal. So one input of the comparator is the fixed DC voltage superposed with an AC component. The microprocessor detects the voltage at the IO port and counts the numbers of voltages read to see if they are equal to the first and second voltages, respectively, during a counting period. The condition of whether the lead wire is in a connected state or disconnected state may be determined by the numbers counted, and a reasonable threshold may be predefined. Counting the number of voltages that are equal to the first and second voltages and determining whether the lead wire is in a connected state or disconnected state may be implemented in various ways.

In a specific embodiment, counting the number of voltages may be achieved by a program in a microprocessor. For example, the microprocessor counts the number of voltages read at the IO port that are equal to the first and second voltages, respectively, during a second time interval. When the number of voltages read that are equal to the first voltage is less than the number of voltages read that are equal to the second voltage, the lead wire is determined to be in a connected state; when the number of voltages read that are equal to the first voltage is greater than or equal to the number of voltages read that are equal to the second voltage, the lead wire is determined to be in a disconnected state.

In another embodiment, counting the number of voltages may be implemented by a counter in the microprocessor. For example, the microprocessor may include a counter and a logic judgment unit. The counter counts the number of first and second voltages read on the IO port, respectively, during the second time interval. The logic judgment unit compares the number of first and second voltages read and determines whether the lead wire is in a connected state or disconnected state by reading the comparison results.

In another embodiment, counting the number may be implemented by a separate hardware counter. The hardware counter counts the number of voltages read at the IO port that are equal to the first and second voltages, respectively, during the second time interval and sends the numbers to the microprocessor. The microprocessor determines whether the lead wire is in a connected state or disconnected state by reading the number of first and second voltages.

When determining whether the lead wire is in a connected state or disconnected state, the microprocessor can compare the number of voltages that are equal to the first voltage with the number of voltages that are equal to the second voltage directly, or it could compare the ratio of the numbers with a threshold. Then, whether the lead wire is in a connected state or disconnected state may be determined by reading the comparison result.

In an embodiment, as shown in FIG. 1, a +3.3V voltage source is added to the signal circuit by a 30 megohm resistance. The +3.3V voltage source, 30 megohm resistance, and a reference lead wire 16 (such as a right leg lead wire) constitute a bias loop. In this embodiment, the threshold is 1.65V, the input of the IO port of the comparator read is 1 when the lead wire is disconnected or 0 when the lead wire is connected, the detecting period is 20 ms, the time interval of reading the input of the IO port is 1 ms, and the input of the IO port read is counted.

1. When the external frequency interference is small and ECG electrodes contact the human body and/or the lead wire well, if the lead wire is in a disconnected state, the number 1 read on the IO port is 20 within 20 ms; if the lead wire is in a connected state, the number 0 read on the IO port is within 20 ms.

Figure 2:
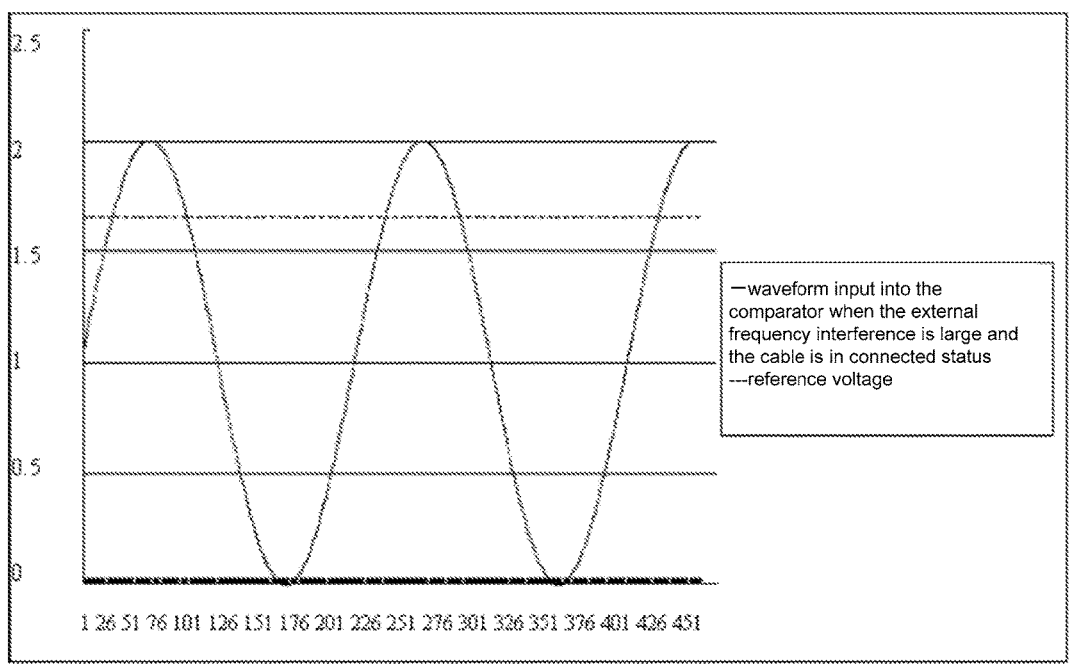
FIG. 2 shows a lead signal inputted into a comparator when a lead wire is in a connected state and external frequency interference is large according to an embodiment.

2. When the external frequency interference is large and the lead wire is in a connected state, the number 0 read on the IO port is greater than the number 1 read on the IO port, and the lead wire is determined to be in a connected state. FIG. 2 shows the relationship between the waveform input into the comparator by the lead wire and the threshold of 1.65V.

Figure 3:
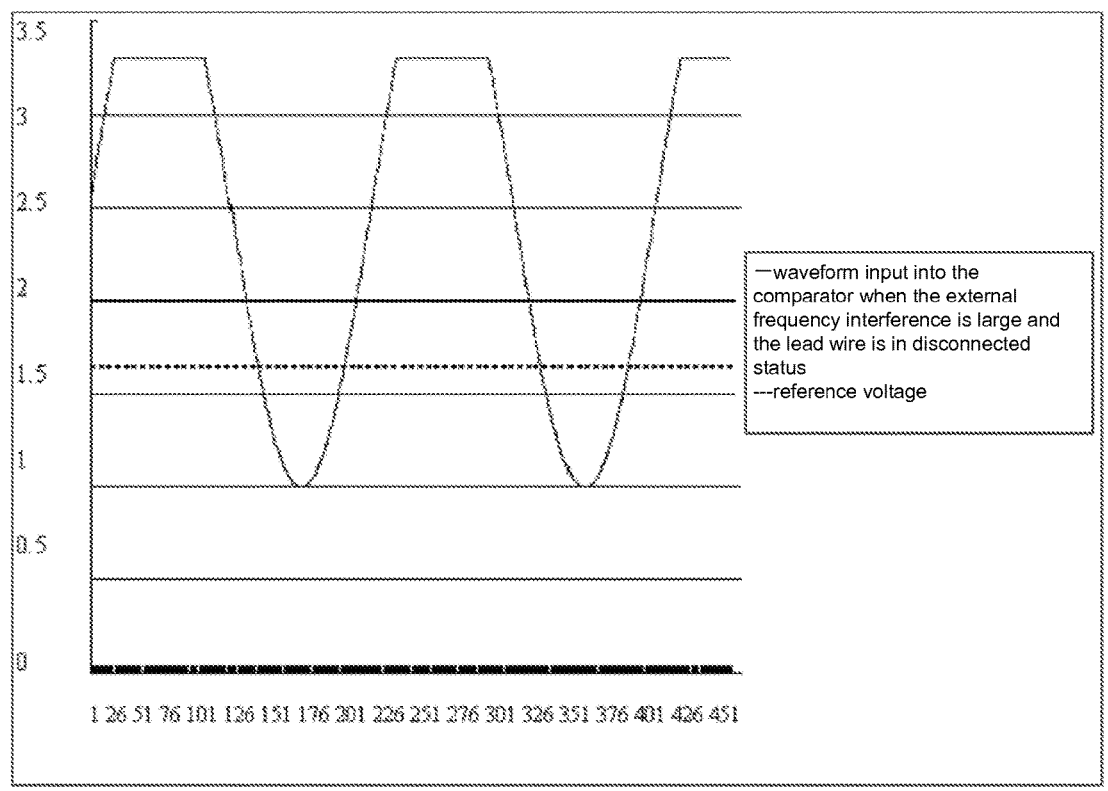
FIG. 3 shows the lead signal inputted into the comparator when the lead wire is in a disconnected state and the external frequency interference is large according to an embodiment.

3. When the external frequency interference is large and the lead wire is in a disconnected state, the number 1 read on the IO port is greater than the number 0 read on the IO port, and the lead wire is determined to be in a disconnected state. FIG. 3 shows the relationship between the waveform input into the comparator and the threshold of 1.65V.

In practical applications, the condition of the lead wire, such as when the lead wire is connected without interference, when the lead wire is connected with large interference, when the lead wire is disconnected without interference, and when the lead wire is disconnected with large interference, may be determined by adjusting the counting thresholds of 0 and/or 1.

Based on the disclosure above, one of ordinary skill in the art will appreciate that the output voltage of the comparator may be set as follows: when the lead signal is greater than or equal to a predefined threshold, the comparator outputs 0 (low voltage); when the lead signal is less than the preset threshold, the comparator outputs 1 (high voltage). The threshold, which is the reference voltage of the comparator, may be preset based on output voltage of the voltage source and judgment tendency.

The number of the lead wires 11 may be one or more, the number of the bias circuits 12 may be one or more, and the number of the comparators 14 may be one or more too. In one embodiment shown in FIG. 1, there are three lead wires 11, three bias circuits 12, three comparators 14, one lead wire 11, one bias circuit 12, and one comparator 14, forming a group. In another embodiment, a different number of comparators 14 may be used, as well as the number of lead wires 11 or bias circuits 12. For example, two lead wires 11 and two bias circuits 12 may be connected to one comparator 14.

Figure 4:
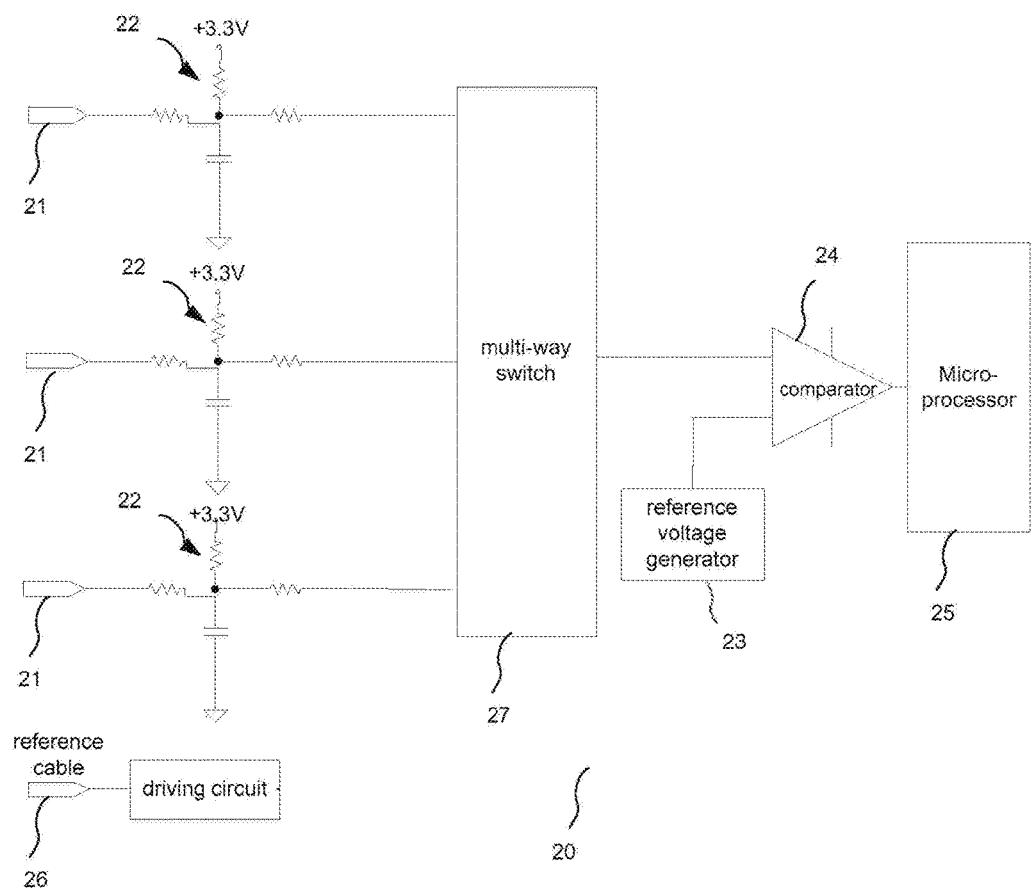
FIG. 4 shows a schematic diagram of the bioelectric signal detecting circuit according to an embodiment.

In another embodiment, as shown in FIG. 4, a different number of comparator may be used. The bioelectric detecting circuit may include lead wires 21, bias circuits 22, and one lead wire detecting circuit 20. The lead wire detecting circuit 20 may include a reference voltage generator 23, a comparator 24, a microprocessor 25 and a multi-way switch 27. One bias circuit 22, one lead wire 21, and one reference lead wire 26 constitute a loop. The multi-way switch 27 has multiple input ends, and each signal output end of the lead wires 21 is connected to one of the input ends, respectively. The output end of the multi-way switch 27 is connected to one input end of the comparator 24. The multi-way switch 27 polls the output end of each lead wire periodically. The other input end of the comparator 24 is connected to the reference voltage generator 23 for accessing reference voltage, and the output end of the comparator 24 is connected to the IO port of the microprocessor 25.

In one embodiment, each lead signal may be sent to the comparator 24 by switching the multi-way switch 27, so all lead signals could share one comparator 14, thus reducing the number of comparators.

The number of comparators 14 may be determined by the number of lead wires 21 and the number of ways in the multi-way switch 27. For example, if there are six lead wires 21 and the multi-way switch 27 is a three-way switch, two comparators 14 are needed.

The lead wire detecting circuit disclosed in the embodiments may be used to detect whether a lead wire in a medical device is in a connected state or disconnected state. For example, it may be used to detect ECG and EEG lead wires, and the medical device may be a patient monitor, an electrocardiograph, or an electroencephalograph. The medical device could also process the lead signals it recognizes—for example, it could amplify the lead signal—and the logic control module could generate images based on the lead signals it recognizes.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, advantages, and solutions to problems have been described above with regard to various embodiments and are not to be construed as critical, required, or essential features or elements. The scope of the present disclosure should, therefore, be determined by the following claims.

What is claimed is:

1. A bioelectric signal detecting circuit, comprising:
   at least one lead wire, which comprises a contact end for contacting a human body and a signal output end;
   at least one bias circuit, wherein each bias circuit corresponds to one of the at least one lead wire and is connected to the signal output end of the one of the at least one lead wire;
   a reference voltage generator for outputting a reference voltage;
   at least one comparator, wherein input ends of the comparator are connected to an output end of the reference voltage generator and the signal output end of the lead wire, respectively, for inputting the reference voltage and lead signal, and the comparator compares the lead signal with the reference voltage and changes output voltage at an output end of the comparator according to a comparison result; and
   a logic control module, wherein an input end of the logic control module is connected to the output end of the comparator, and the logic control module determines whether the lead wire is in a connected state or disconnected state according to at least the output voltage at the output end of the comparator,
   wherein the logic control module comprises a microprocessor, which comprises a counter and a logic determination unit, where the counter counts a number of voltages read at an IO port that are equal to a first voltage and a second voltage, respectively, during a time interval, and the logic determination unit compares the number of voltages read at the IO port that are equal to the first voltage with the number of voltages read at the IO port that are equal to the second voltage and determines whether the lead wire is in a connected state or disconnected state according to the comparison result.

2. A lead wire detecting circuit, comprising:
a reference voltage generator for outputting a reference voltage;
at least one comparator, wherein input ends of the comparator are connected to an output end of the reference voltage generator and a signal output end of a lead wire, respectively, for inputting a reference voltage and a lead signal, and the comparator compares the lead signal with the reference voltage and changes an output voltage at an output end of the comparator according to a comparison result; and
a logic control module, wherein an input end of the logic control module is connected to the output end of the comparator, and the logic control module determines whether the lead wire is in a connected state or disconnected state according to the output voltage at the output end of the comparator,
wherein the logic control module comprises a microprocessor, which comprises a counter and a logic determination unit, where the counter counts a number of voltages read at an IO port that are equal to a first voltage and a second voltage, respectively, during a time interval, and the logic determination unit compares the number of voltages read at the IO port that are equal to the first voltage with the number of voltages read at the IO port that are equal to the second voltage and determines whether the lead wire is in a connected state or disconnected state according to the comparison result.

3. The lead wire detecting circuit of claim 2, wherein the TO port of the microprocessor is connected to the output end of the comparator, and the microprocessor reads a voltage at the IO port in the time interval and determines whether the lead wire is in a connected state or disconnected state according to the voltage read.

4. The lead wire detecting circuit of claim 3, wherein the microprocessor determines the lead wire is in a disconnected state when the voltage read at the IO port is equal to the first voltage and determines the lead wire is in a connected state when the voltage read at the IO port is equal to the second voltage; or
the microprocessor counts the number of voltages read at the IO port that are equal to the first and second voltages, respectively, during a second time interval, and when the number of voltages read at the IO port that are equal to the first voltage is less than the number of voltages read at the IO port that are equal to the second voltage, the microprocessor determines the lead wire is in a connected state; when the number of voltages read at the IO port that are equal to the first voltage is greater than or equal to the number of voltages read at the IO port that are equal to the second voltage, the microprocessor determines the lead wire is in a disconnected state.

5. The lead wire detecting circuit of claim 2, wherein the reference voltage is preset according to the output voltage of the bias circuit and judgment tendency.

6. The lead wire detecting circuit of claim 2, wherein the number of comparators is equal to the number of lead wires, and there is a one-to-one correspondence between the comparators and the lead wires.

7. The lead wire detecting circuit of claim 2, wherein the lead wire detecting circuit further comprises a multi-way switch, wherein input ends of the multi-way switch are connected to the signal output end of each lead wire, respectively, an output end of the multi-way switch is connected to one of the input ends of the comparator, and the multi-way switch polls the output end of each lead wire.

8. A medical device, comprising:
at least one lead wire, which comprises a contact end for contacting with a human body and a signal output end;
at least one bias circuit, wherein each bias circuit corresponds to one of the at least one lead wire and is connected to the signal output end of the one of the at least one lead wires; and
a lead wire detecting circuit comprising:
   a reference voltage generator for outputting a reference voltage;
   at least one comparator, wherein input ends of the comparator are connected to an output end of the reference voltage generator and an signal output end of a lead wire, respectively, for inputting a reference voltage and a lead signal, and the comparator compares the lead signal with the reference voltage and changes an output voltage at an output end of the comparator according to the comparison result; and
   a logic control module, wherein an input end of the logic control module is connected to the output end of the comparator, and the logic control module determines whether the lead wire is in a connected state or disconnected state according to the output voltage at the output end of the comparator,
   wherein the logic control module comprises a microprocessor, which comprises a counter and a logic determination unit, where the counter counts a number of voltages read at an IO port that are equal to a first voltage and a second voltage, respectively, during a time interval, and the logic determination unit compares the number of voltages read at the IO port that are equal to the first voltage with the number of voltages read at the IO port that are equal to the second voltage and determines whether the lead wire is in a connected state or disconnected state according to the comparison result.

9. The medical device of claim 8, wherein the medical device comprises one of a patient monitor, an electrocardiograph, or an electroencephalograph.

* * * * *